United States Patent
Berlinger et al.

(10) Patent No.: US 11,865,368 B2
(45) Date of Patent: Jan. 9, 2024

(54) TRACKING SOFT TISSUE IN MEDICAL IMAGES

(71) Applicant: Brainlab AG, Munich (DE)

(72) Inventors: Kajetan Berlinger, Munich (DE); Stephan Froehlich, Aschheim (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 18/123,117

(22) Filed: Mar. 17, 2023

(65) Prior Publication Data
US 2023/0230236 A1    Jul. 20, 2023

Related U.S. Application Data

(63) Continuation of application No. 15/121,763, filed as application No. PCT/EP2014/053760 on Feb. 26, 2014, now abandoned.

(51) Int. Cl.
*A61N 5/10*    (2006.01)
*A61B 6/02*    (2006.01)
(Continued)

(52) U.S. Cl.
CPC ........... *A61N 5/1049* (2013.01); *A61B 6/022* (2013.01); *A61B 6/032* (2013.01); *A61B 6/5223* (2013.01);
(Continued)

(58) Field of Classification Search
CPC ......... G06T 7/0012; G06T 2207/10081; G06T 2207/30061; G16H 30/40
See application file for complete search history.

(56) References Cited

U.S. PATENT DOCUMENTS 6,019,724 A    2/2000    Gronningsaeter et al.
6,144,875 A    11/2000    Schweikard et al.
(Continued)

FOREIGN PATENT DOCUMENTS

WO    2015127970    9/2015

OTHER PUBLICATIONS

European Patent Office, International Search Report for PCT/EP2014/053760 dated Oct. 10, 2014.
(Continued)

*Primary Examiner* — Keith M Raymond
*Assistant Examiner* — Sean A Frith
(74) *Attorney, Agent, or Firm* — Gray Ice Higdon

(57) ABSTRACT

The present invention relates to a medical data processing method of determining the representation of an anatomical body part (2) of a patient (1) in a sequence of medical images, the anatomical body part (2) being subject to a vital movement of the patient (1), the method being constituted to be executed by a computer and comprising the following steps:
a) acquiring advance medical image data comprising a time-related advance medical image comprising a representation of the anatomical body part (2) in a specific movement phase;
b) acquiring current medical image data describing a sequence of current medical images, wherein the sequence comprises a specific current medical image comprising a representation of the anatomical body part (2) in the specific movement phase, and a tracking current medical image which is different from the specific current medical image and comprises a representation of the anatomical body part (2) in a tracking movement phase which is different from the specific movement phase;

(Continued)

c) determining, based on the advance medical image data and the current medical image data, specific image subset data describing a specific image subset of the specific current medical image, the specific image subset comprising the representation of the anatomical body part (2);

d) determining, based on the current medical image data and the image subset data, subset tracking data describing a tracked image subset in the tracking current medical image, the tracked image subset comprising the representation of the anatomical body part (2).

15 Claims, 3 Drawing Sheets

(51) Int. Cl.
| | |
|---|---|
| *A61B 6/03* | (2006.01) |
| *A61B 6/00* | (2006.01) |
| *G06T 7/11* | (2017.01) |
| *G06T 7/73* | (2017.01) |
| *G06T 7/246* | (2017.01) |
| *G16H 50/50* | (2018.01) |
| *G16H 30/40* | (2018.01) |
| *G06T 7/00* | (2017.01) |

(52) U.S. Cl.
CPC .......... *A61B 6/5235* (2013.01); *A61B 6/5264* (2013.01); *A61B 6/5288* (2013.01); *A61B 6/541* (2013.01); *A61N 5/107* (2013.01); *A61N 5/1067* (2013.01); *A61N 5/1068* (2013.01); *G06T 7/0012* (2013.01); *G06T 7/0014* (2013.01); *G06T 7/11* (2017.01); *G06T 7/248* (2017.01); *G06T 7/73* (2017.01); *G16H 30/40* (2018.01); *G16H 50/50* (2018.01); *A61B 6/487* (2013.01); *A61N 2005/1061* (2013.01); *G06T 2207/10021* (2013.01); *G06T 2207/10081* (2013.01); *G06T 2207/10124* (2013.01); *G06T 2207/20104* (2013.01); *G06T 2207/30061* (2013.01)

(56) References Cited

U.S. PATENT DOCUMENTS

| | | |
|---|---|---|
| 6,501,981 B1 | 12/2002 | Schweikard et al. |
| 7,349,522 B2 * | 3/2008 | Yan ................. G01N 23/223 378/65 |
| 2004/0081269 A1 | 4/2004 | Pan et al. |
| 2004/0092815 A1 | 5/2004 | Schweikard et al. |
| 2004/0116804 A1 | 6/2004 | Mostafavi |
| 2006/0074292 A1 | 4/2006 | Thomson et al. |
| 2008/0033784 A1 | 2/2008 | Chalimadugu et al. |
| 2013/0266202 A1 | 10/2013 | Yamada et al. |
| 2014/0029812 A1 * | 1/2014 | Kriston ................. G06T 7/70 382/128 |
| 2014/0275704 A1 | 9/2014 | Zhang et al. |
| 2014/0275962 A1 * | 9/2014 | Foo ................. A61B 5/055 600/411 |
| 2017/0065832 A1 | 3/2017 | Berlinger et al. |

OTHER PUBLICATIONS

European Patent Office; Decision to Grant issued for Application No. 14708825.6, 2 pages, dated Sep. 13, 2018.

* cited by examiner

TRACKING SOFT TISSUE IN MEDICAL IMAGES

The present invention relates to a medical data processing method of determining the representation of an anatomical body part of a patient in a sequence of medical images, wherein the anatomical body part is subject to a vital movement of the patient. The data processing method is preferably constituted to be executed by a computer. The invention therefore also relates to a corresponding computer program and a computer executing that program.

When executing medical procedures such as radiosurgery or radiotherapy in particular outside of the head (so-called extra-cranial radiosurgery or radiotherapy), for example in order to deliver a desired radiation dose to a target region including in particular a tumour which is located in soft tissue (such as lung tissue or tissue of other internal organs), it is in general necessary to consider a vital movement of such a target region in order to support continuous irradiation of the target region and avoid irradiation of off-target regions such as organs at risk which shall not be damaged. Such vital movements are in particular periodic and due to for example a shift of organ tissue caused by for example breathing motion of the thorax, the beating motion of the heart or movements of other internal organs such as the intestines. Further explanations as to the origin and consequences of vital movements are also disclosed in EP 2 189 943 A1 and EP 2 189 940 A1, also published as US 2010/0125195 A1 and US 2010/0160836 A1, respectively.

When conducting one of for example the aforementioned medical procedures, it is often desirable to have a visual guidance for the position of the soft tissue which is subject to the vital movement.

In this regard, the "Xsight Lung Tracking System" produced by Accuray Inc. provides for a superposition and fusion, respectively, of DRRs to corresponding X-ray images in order to compare the current position of the soft tissue to be tracked (defined by the X-ray images) with its planned position (defined by the DRRs which are gathered from a pre-acquired planning computed tomography). However, visually inspecting the fusion between a digitally rendered radiograph (DRR) that focusses on soft tissue and a conventional X-ray image is difficult and time-consuming, and thus hardly feasible without applying an automated process. Furthermore, such an automatic multi-modal fusion (i.e. fusion between images generated by applying different medical imaging modalities) lacks robustness. Besides that, the information contained in the DRRs is out of date and therefore a comparison of each one of a plurality of DRRs with a (single) X-ray image may lead to erroneous results.

The following documents are of general relevance to the field of technology to which the present invention relates: US 2008/00337843 A1, U.S. Pat. No. 6,501,981 B1, 6,144,875 A.

A problem to be solved by the present invention therefore is to provide an improved method and apparatus for tracking the position of moving soft tissue in a series of X-ray images.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention shall primarily be used in particular within the Vero® radiosurgery system provided by Brainlab AG. Vero® provides high accuracy for treatment delivery, even with moving targets. Core features, such as sophisticated and versatile image-guidance, verification tools and the first-of-its-kind gimbaled irradiation head with tilt functions for isocentric and non-isocentric treatments deliver targeting confidence. With built-in fluoroscopy, tumor areas can be treated dynamically in real time even as they move in parallel with breathing and digestion with uninterrupted beam delivery. Vero® possesses an innovative imaging feedback system to deliver high quality, targeted and truly individualized treatments. Furthermore, Vero® provides the following advantageous capabilities:

- Enables confident treatment of moving targets and high accuracy dose delivery
- Motion management with versatile image guidance and verification tools and gimbaled irradiation head with tilt functions for isocentric and non-isocentric treatments
- Uninterrupted dynamic moving tumor treatment with proprietary real-time stereo fluoroscopy
- Targeted, individualized delivery of treatments with continuous tracking; incorporates anatomical changes and breathing cycles with closed-loop feedback system

EXEMPLARY SHORT DESCRIPTION OF THE PRESENT INVENTION

In the following, a short description of specific features of the present invention is given which shall not be understood to limit the invention only to the features or a combination of the features described in this section.

The present invention is directed in particular to a data processing method (e.g. a computer program) for tracking an anatomical body part, such as the diaphragm or a tumour, in a series of x-ray images. The anatomical body part moves due to e.g. a vital movement such as breathing motion of the thorax. The anatomical body part is defined in a CT image acquired beforehand and being associated with a known movement phase (e.g. full inspiration or full expiration) during the vital movement. Then, the series of x-ray images of the (still moving) anatomical body part is taken. An aim of the invention is to track and advantageously visually highlight the anatomical body part throughout the series of x-ray images. A problem may, however, occur in doing so since the representation (e.g. visual impression) of the anatomical body part may not be comparable between the pre-acquired CT image and an arbitrary one of the series of x-ray images. Thus, the movement phase associated with each one of the x-ray images is determined. According to one solution, this is done by tracking the thoracic movement using external infrared-reflecting markers and a navigation system while taking the series of x-ray images and time-stamping the x-ray images and the positional information for the thorax gathered from tracking. The time stamps relate each one of the x-ray images with a specific movement phase of the thorax. The specific x-ray image being associated with the same movement phase as the CT image can therefore be determined, and the representation of the anatomical body part defined in the CT image can be determined in the x-ray image by comparing the CT image with the specific x-ray image, for example by fusing the CT image to the specific x-ray image. The specific x-ray image is then compared to the other x-ray images (e.g. by fusing the specific x-ray image to the other x-ray images) to find the anatomical body part in those x-ray images and preferably highlight it to be easily recognized by a user.

The invention also relates to a computer configured to execute a corresponding computer program. Furthermore, the invention relates to a treatment device (for example, a radiotherapy device or radiosurgery device) comprising such a computer.

GENERAL DESCRIPTION OF THE PRESENT INVENTION

In this section, a description of the general, in particular preferred, features of the invention is given.

In order to solve the aforementioned problem, in particular a data processing method, more particularly a medical data processing method (i.e. a data processing method for use in relation to a medical environment), of determining the representation of an anatomical body part of a patient in a sequence of medical images is provided. The anatomical body part is subject to in particular a vital movement of the patient (i.e. of a vital movement of at least one body part of the patient) and may be any anatomical body part. In particular, the anatomical body part comprises a tumour and may therefore constitute a target region on which the envisaged medical procedure such as radiotherapy or radiosurgery may be carried out. In particular, the anatomical body part represents a soft tissue body part such as skin, or tissue constituting an internal organ such as the stomach, the heart, the liver, the diaphragm or the lung. A soft-tissue body part differs from a hard tissue body part (such as bone or cartilage) in particular in respect of its absorption for imaging radiation (such as electromagnetic waves in the magnetic resonance spectrum used for magnetic resonance imaging, ultrasound imaging radiation or ionizing imaging radiation such as x-rays). In general, the absorption of for example ionizing imaging radiation is lower in soft tissue than in hard tissue.

The method is preferably constituted to be executed by a computer. In particular, the computer may execute all or less than all of the steps of the disclosed method. Preferably, at least one step of the disclosed method is executed by a computer. The disclosed method comprises the following preferable steps and features.

Preferably, advance medical image data is acquired which comprises a time-related advance medical image. The advance medical image comprises and in particular defines (more particularly, represents and/or is) a representation of the anatomical body part in a specific movement phase. The advance medical image preferably is time-related, i.e. the image information contained in the advance medical image is associated with time information such as a point in time, for example absolute time or relative to a specific starting point in time. The specific movement phase corresponds to a specific movement state in the vital movement which the anatomical body part is subject to. In particular, the anatomical body part moves due to the vital movement and thereby passes through a plurality of movement states during the vital movement. Since the vital movement is in particular cyclic (periodic), each movement state may be associated with a specific movement phase. For example, the anatomical body part is the diaphragm which is subject to the thoracic breathing movement as a vital movement. A specific movement phase may then define states of e.g. inspirational movement or expirational movement (for example a specific movement phase may be complete inspiration or complete expiration). The advance medical image is time-related in order to associate the representation of the anatomical body part with the specific movement phase.

Preferably, the advance medical image data has been generated in particular before execution of the disclosed method by detecting the vital movement for example based on tracking marker devices attached to the patient's body and correlating the result of the tracking (i.e. the resulting positional measurements) with medical image data serving as a basis for generating the advance medical image, for example with a pre-acquired computed tomography which is used in particular for planning the envisaged medical procedure to be carried out on the patient). The markers are preferably retroreflective markers which are able to reflect infrared electromagnetic radiation, the reflections being detected by a detection unit (e.g. a stereoscopic camera) of a navigation system and transformed into digital signals which indicate the positions of the markers. For example, the vital movement is the aforementioned breathing movement and the anatomical body part is the diaphragm. A breathing curve of the breathing movement of the diaphragm is generated for example by attaching retroreflective markers to the patient's thorax and acquiring a sequence of computed tomography (CT) images while tracking and recording the positions and/or positional changes of the markers during the breathing movement. Thereby, each representation of the diaphragm in a single CT image may be associated with a specific movement state (i.e. in particular position) of the markers and thereby specific movement phase of the diaphragm. The breathing curve then describes (in particular represents) the position of the thorax (in particular, its geometry, for example volume) in dependence on time. In particular, the advance medical image is associated with a specific point (in particular point in time) on the breathing curve. Further particularly, the advance medical image is associated with a specific movement phase in the period of the vital movement, i.e. in the breathing period. The term of marker and how the position of a marker can be determined is explained further below in the section "Definitions".

The advance medical image preferably is at least one digitally rendered radiograph (DRR), in particular a pair of digitally rendered radiographs (DRRs), rendered from a CT image of the anatomical body part. In this context, the term of "image" encompasses also a pair of images which are oriented in viewing directions which are preferably perpendicular to each other.

In the framework of the present disclosure, the term of representation encompasses the visual impression which the anatomical body part generates in a specific image (for example, in the advance medical image or the current medical image or the tracked image subset or the tracking current medical image which are mentioned below). The term of representation therefore encompasses graphic, in particular geometric and colour features, of the image of the anatomical body part. For example, the term of representation encompasses contrast values, and colours in the respective medical image.

Preferably, current medical image data is acquired which describes (in particular defines, more particularly represents and/or comprises) a sequence of current medical images. The current medical images are preferably x-ray images (generated for example using a fluoroscope, and thus representing a sequence of fluoroscopic x-ray images). The current medical images preferably are each at least one (e.g. fluoroscopic) x-ray image (as an example, each current medical image comprises, in particular consists of, a pair of stereo-x-ray images) of the anatomical body part. In this context, the term of "image" encompasses also a pair of images which are oriented in viewing directions which are preferably perpendicular to each other. The sequence comprises a specific current medical image, in particular at least one such specific current medical image. The current medical image comprises (in particular defines, more particularly represents and/or is) a representation of the anatomical body part in the specific movement phase. The specific movement phase is at least substantially the same as (i.e. in a preferred embodiment, it is the same as and/or identical to) the specific movement phase defined by the representation of the anatomical body part in the advance medical image. The current medical image data furthermore describes (in particular defines, more particularly represents and/or comprises) at least one tracking current medical image, preferably a plurality of tracking current medical images. Each tracking current medical image is preferably different from the specific current medical image, and comprises (in particular defines, more particularly represents and/or is) a representation of the anatomical body part in the movement phase (also called tracking movement phase) which is different from the specific movement phase. In particular, the tracking movement phase and the specific movement phase are not identical.

Preferably, the advance medical image data has been generated by applying a computed tomography imaging method to the patient's body and the advance medical image is in particular a digitally rendered radiograph rendered from the computer tomography of the patient's body. Further preferably, the sequence of current medical images has been generated by applying an x-ray imaging method (in particular a conventional x-ray imaging method) such as a stereo-x-ray-imaging method (e.g. using the aforementioned fluoroscope) to the patient's body. However, it is also within the framework of this disclosure that the sequence of current medical images (i.e. both the at least one specific current medical image and the at least one tracking current medical image) have been generated by another medical imaging method, in particular not by x-ray imaging.

Preferably, specific image subset data is determined based on the (in particular from) the advance medical image data and the current medical image data. The specific image subset data describe (more particularly, represents and/or is) in particular a specific image subset of the specific current medical image. The image subset is preferably a "real" subset of the specific current medical image, i.e. it comprises (in particular consists of, i.e. comprises only) image information from the specific current medical image which is less than the total image information contained in the specific current medical image. However, the image subset comprises at least the representation of the anatomical body part in the specific medical image. The current medical image is preferably determined by comparing the advance medical image to the sequence of current medical images and finding the current medical image comprising a representation of the anatomical body part which best matches the representation of the anatomical body part in the advance medical image. It is general to be assumed that this best match is achieved when the anatomical body part in the representation of the advance medical image and in the representation of the current medical image has the same movement state, and if specific current medical image and the advance medical image describe in particular the same (namely the specific) movement phase.

Preferably, the specific image subset data is determined for exactly one (i.e. only one) of the current medical images. This approach allows for an efficient procedure in first of all determining the image region in the specific current medical image to be tracked and by applying knowledge about this region to the at least one tracking current medical image.

The comparison between the sequence of current medical images and the advance medical images is preferably performed by applying an image fusion algorithm to the advance medical image and the sequence of current medical images to find the specific current medical image, i.e. the member of the sequence of current medical images which best fits to the advance medical image based on fusing the advance medical image to each one of the sequence of current medical images. The image fusion algorithm may be constituted to conduct an elastic or a rigid image fusion. Elastic image fusion allows for deformation of geometries, rigid image fusion does not involve a deformation of geometry. In particular, the specific current medical image is the member of the sequence of the current medical images which is most similar to the advanced medical image. The terms of image fusion and similarity are explained further below in the section "Definitions" within the explanation relating to image fusion. In order to successfully perform the image fusion between the advance medical image and the sequence of current medical images, it is preferred that the current medical image data and the advance medical image data have been generated by applying a medical imaging modality for generating the respective dataset which in the case of both datasets underlies the at least substantially same absorption of the imaging radiation by the anatomical body part. For example, the advance medical image data has been generated by applying an x-ray-based computed tomography imaging modality, and the current medical image data has been generated by applying an x-ray imaging modality. Since both these modalities use x-rays for imaging the anatomical body part, the absorption values of the imaging radiation is comparable if not the same in both the case of generating the advance medical image data and the current medical image data.

Preferably, the specific image subset data is determined based on (in particular by) in particular automatically or manually determining a corresponding representation of the anatomical body part in the advance medical image and the specific current medical image. Corresponding representation in this sense means that the representations of the anatomical body part in both images are similar to each other at least to a predetermined extent. This similarity is determined as explained above according to one specific embodiment automatically determined by applying an image fusion algorithm to the advance medical image and the specific current medical image. A region in the specific current medical image for which the similarity has been determined is then for example selected and in particular outlined and/or highlighted in the specific current medical image.

According to an alternative and specific preferred embodiment, current medical image user input data is acquired which describes (in particular defines and/or represents) an input (in particular information gathered from an input) by a user. The input is for example a manual input. Furthermore, the input is suitable for selecting the specific image subset from the specific current medical image. For example, the user may operate a touchscreen to delimit the specific image subset from the specific current medical image which has beforehand been determined to contain the representation of the anatomical body part which is (within the sequence of current medical images) most similar to the representation of the anatomical body part in the advance medical image. Alternatively or additionally, the user may operate a pointing and input equipment for selecting the specific image subset, such as mouse or a trackball to define the specific image subset on a visual indicating means such as a monitor displaying the specific current medical image. The selected image information defines the specific image subset (in particular, the specific image subset consists of the clipped image information).

According to an alternative embodiment, advance image subset data is acquired which describes an advance image subset of the image information contained in the advance medical image. As explained with regard to the specific image subset, the advance image subset also is a "real" subset of the advance medical image. In particular, the advance image subset comprises (in particular consists of, i.e. comprises only) image information contained in the advance medical image and less image information than the total image information contained in the advance medical image. The advance image subset comprises the representation of the anatomical body part in the advance medical image. The advance image subset data can also be generated and acquired on the basis of user input as explained with regard to the current medical image user input data. In the case of user input for acquiring the advance image subset data, preferably advance medical image user input data is acquired which describes the required input by a user. The details of such a user input are in particular the same as for the user input used for acquiring the current medical image user input data with the exception that the user input is executed on the advance medical image and not on the specific current medical image. The advance image subset data is then determined based on the advance medical image user input data.

As an alternative to user input for defining the specific image subset and/or the advance image subset, at least one (preferably both) of the advance image subset and the specific image subset can be determined by applying an image segmentation algorithm (for example, an edge detection algorithm) to the respective one of the advance medical image and/or the specific current medical image. As an even further feature, the specific image subset can be determined by matching the current medical image data with an atlas, e.g. by image fusion between the current medical image data and an atlas. An atlas is understood to be a model of a patient's body which has been generated by statistical analysis of medical images taken for a plurality of patient bodies. For example, an anatomical body part to be included in the specific image subset can be defined in the atlas and the current medical image data can be matched with the atlas to determine the specific image subset which includes the representation of that anatomical body part. The anatomical body part may be for example an indicator body part indicating the specific movement phase (e.g. the diaphragm if the vital movement is a breathing movement). In an even further embodiment, matching the atlas with the current medical image data can be combined with a user input or an image segmentation algorithm for defining the specific image subset. For example, that matching with the atlas may be conducted subsequently to the user input or to execution of the image segmentation algorithm in order to check whether the specific image subset thus determined actually includes a representation of the anatomical body part selected from (in) the atlas.

It is notable that the above-described embodiments for using user input or automatic determination for defining the advance image subset and/or the specific image subset may also be combined. For example, first an automatic determination of the advance image subset and/or the specific image subset may be performed, followed by a manual correction of the automatic determination result (e.g. of the segmentation result) by user input. For example, the user may wish to increase or decrease the extent of the specific image subset and/or the advance image sub set.

The specific image subset data may according to a further embodiment also be determined based on the result of comparing the advance image subset to the specific current medical image. For example, an image fusion algorithm may be applied to the specific image subset to fuse it to the specific current medical image (i.e. an image fusion algorithm may be applied to the advance image subset data and the current medical image data describing—in particular defining, more particularly representing and/or being—the specific current medical image) in order to determine the region in the specific current medical image which is most similar to the advance image subset. Thereby, the specific image subset is determined.

Preferably, subset tracking data is determined based on (in particular from) the current medical image data and the image subset data. The subset tracking data describes (in particular defines, more particularly represents and/or is) a tracked image subset in the tracking current medical image. The tracked image subset comprises (in particular defines, more particularly represents and/or is) the representation of the anatomical body part in the tracking current medical image. In the case of the current medical image data describing more than one tracking current medical image, the tracked image subset is determined for each one of the tracking current medical images. For example, the sequence of current medical images (in particular, all current medical images which are not identical to the specific current medical image) are searched for image information which is at least to a predetermined extent comparable (in particular similar) to the specific image subset. For example, the specific image subset data can be fused (by conducting an elastic or rigid image fusion algorithm) to the other members of the sequence of the current medical images (in particular to the at least one tracking current medical image) in order to determine a region in the tracking current medical image which contains the representation of the anatomical body part which is at least to a predetermined degree comparable (in particular similar) to the specific image subset. This region then is determined to be the tracked image subset.

Preferably, the specific image subset data describes (in particular contains information defining, more particularly representing and/or being) the position of the specific image subset in the specific current medical image. Further preferably, the subset tracking data describes (in particular contains information defining, more particularly representing and/or being) the position of the tracked image subset in the tracking current medical image. In particular, the specific image subset data and the subset tracking data, respectively, contain information defining the pixel coordinates of the specific image subset and the tracked image subset, respectively, in the specific current medical image and the tracking current medical image, respectively. This allows to extract the medical image information making up the specific image subset from the specific current medical image in order to perform the comparison with (in particular fusion to) the at least one tracking current medical image for determining the tracked image subset. In particular, positions (i.e. pixel coordinates) in the tracking current medical image having the same values as the position (i.e. pixel coordinates) of the specific image subset are analyzed with respect to the degree of similarity to the specific image subset. Alternatively, the specific image subset may be compared to the total image information contained in the tracking current medical image in order to determine the region in the tracking current medical image which fulfils the conditions for similarity to the specific image subset. In this approach, it is not necessary to know the position of the specific image subset in the specific current medical image. Therefore, the tracking current medical image is searched for a region which is similar to the specific image subset. In other words, the subset tracking data is determined preferably by determining a region in the tracking current medical image which is at least to a predetermined degree comparable to the specific image subset.

The disclosed method comprises a further preferred step of determining display marking data based on (in particular from) the specific image subset data and the tracking image subset data. The display marking data describes (in particular defines, more particularly represents and/or is) a graphical feature for marking the positions of the specific image subset and the tracking image subset in in particular a graphical rendering of the specific current medical image and the tracking current medical image, respectively. This allows for supplying the user with visual information such as for example a frame which is highlighted around the anatomical body part so as to simplify visual tracking of its vital movement.

Preferably, the disclosed method comprises a step of determining internal breathing curve data based on (in particular from) the current medical image data and the subset tracking data and current movement phase data. The properties of the current movement phase data shall be described further below. The internal breathing curve data describes (in particular defines, and more particularly represents and/or is) a time-correlation of the image positions of the anatomical body part and the sequence of medical images. In particular, each one of the sequence of the medical images is assigned to a specific movement phase of the anatomical body part. Thereby, an internal breathing curve of the anatomical body part can be established by having a (in particular only one) advance medical image which is associated with a known specific movement phase of the anatomical body part, finding the corresponding current medical image under the assumption that it is associated also with the specific movement phase, and tracking the representation of the anatomical body part in that current medical image in the other members of the sequence of current medical images (i.e. in the at least one tracking current medical image).

In an advantageous embodiment, generation of the internal breathing curve data is supported by acquiring the aforementioned current movement phase data. The current movement phase data describes (in particular defines, more particularly represents and/or is) a current movement phase of the anatomical body part in the states in which it is described (i.e. depicted) by the sequence of current medical images. The current movement phase data is generated for example based on (in particular by) acquiring digital signals which describe the vital movement. Such digital signals have been generated preferably based on (in particular by) for example tracking marker devices attached to the patient's body and correlating (in particular time-correlating) the result of the tracking (i.e. the positional measurements gained thereby) with the current medical image data. In particular, each one of the current medical images is associated with a specific point on the movement curve defining the vital movement, in the case of the vital movement being the breathing movement of the patient, for example on the breathing curve. The specific current medical image is then preferably determined based on the current movement phase data. In particular, the time information with which the current medical image data is associated serves as a basis for selecting the current medical image (i.e. the specific current medical image) which is associated with the same movement phase as the advance medical image, i.e. with the specific movement phase (defining the same point on the vital movement curve, for example on the breathing curve). This avoids having to assert the whole sequence of the current medical images for a representation of the anatomical body part in the specific movement phase in order to determine the specific current medical image.

The current medical image data is according to an alternative embodiment of the disclosed method not acquired while tracking a vital movement using markers and a navigation system for tracking the markers. Rather, the current medical image data is acquired at specific (discrete) points in time during a cycle of the vital movement, for example during one breathing cycle (breathing period) in the case of the vital movement being a breathing movement. Thus, it is ensured that the current medical image data comprises a representation of the anatomical body part in both the specific movement phase and the tracking movement phase. The explanations regarding the technical meaning of the specific movement phase are in general also valid for the tracking movement phase with the exception that the tracking movement phase is not identical to the specific movement phase.

The inventions provides the advantage of being able to track a moving anatomical body part in a series of x-ray images outgoing from a CT image of the anatomical body part without having to conduct a plurality of image fusion procedures between images of different medical imaging modalities (i.e. multi-modal image fusions, which are known to be complicated and prone to data processing faults), i.e. between a plurality of CT images and each at least one x-ray image. Rather, such a multi-modal image fusion is conducted only once between the advance medical image and at least one current medical image (e.g. an x-ray image), preferably only one current medical image which is known to be the specific current medical image from e.g. tracking the patient's vital movement while generating the current medical image data). Tracking the anatomical body part in the remaining images of the sequence of current medical images (x-ray-images) is then done by conducting mono-modal image fusion procedures between the current medical images (e.g. between the specific current medical image and the at least one tracking current medical image) which were all generated using the same medical imaging modality (namely x-ray). Thereby, problems associated with conducting multi-modal image fusion are avoided.

The invention also relates to a program which, when running on a computer, causes the computer to perform one or more or all of the method steps described herein and/or relates to a program storage medium on which the program is stored (in particular in a non-transitory form) and/or relates to a computer comprising said program storage medium and/or relates to a (physical, in particular electrical, in particular technically generated) signal wave, in particular a digital signal wave, carrying information which represents the program, in particular the aforementioned program, which in particular comprises code means which are adapted to perform any or all of the method steps described herein.

The invention also relates to a treatment device, which is at least one of for example a radiotherapy device and a radiosurgery device, comprising:

a) the aforementioned computer which is in particular configured to execute the aforementioned program which, when running on the computer or when loaded onto the computer (in particular into the memory of the computer), causes the computer to perform the method steps of the above-described method;

b) a medical imaging device for acquiring the current medical image data, wherein the medical imaging device is for example an x-ray imaging device or a CT imaging device (a computer tomograph);

c) an irradiation unit for emitting a treatment beam to the patient's body, wherein the irradiation unit is at least one of a particle accelerator, a high-energy x-ray-tube and a radioactive substance which emits preferably gamma radiation.

The computer of the radiotherapy and/or radiosurgery device is preferably operatively coupled to the medical imaging device to acquire the current medical image data. Furthermore, it is preferably operatively coupled to the irradiation unit to issue control signals to the irradiation unit for emitting the treatment beam. In particular, the computer is configured to activate the irradiation unit based on the current movement phase data. For example, the computer may determine whether the current movement phase data indicates that the current movement phase is a predetermined movement phase at which the target region (which according to a particular embodiment coincides with the anatomical body part) shall be irradiated, and the treatment beam is then activated.

In particular, the invention does not involve or in particular comprise or encompass an invasive step which would represent a substantial physical interference with the body requiring professional medical expertise to be carried out and entailing a substantial health risk even when carried out with the required professional care and expertise. In particular, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or in particular comprise or encompass any surgical or therapeutic activity. The invention is instead directed in particular to positioning the tool relative to the medical implant, which may be outside the patient's body. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which in particular comprises technical, in particular tangible components, in particular mechanical and/or electronic components. Any device mentioned as such in this document is a technical and in particular tangible device.

The method in accordance with the invention is in particular a data processing method. The data processing method is preferably performed using technical means, in particular a computer. The data processing method is preferably constituted to be executed by or on a computer and in particular is executed by or on the computer. In particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or which are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer.

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are in particular designed to enable a seamless transition from one dataset (for example a first dataset such as for example a first image) to another dataset (for example a second dataset such as for example a second image). The transformation is in particular designed such that one of the first and second datasets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field. These vectors are determined by the optimisation algorithm in such a way as to result in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). These constraints include in particular the constraint that the transformation is regular, which in particular means that a Jacobian determinant calculated from a matrix of the deformation field (in particular, the vector field) is larger than zero, and also the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than one tenth or one hundredth or one thousandth of the diameter of the image, and in particular about equal to or less than the distance between neighbouring voxels. Large deformations can be implemented, in particular due to a high number of (iteration) steps.

The determined elastic fusion transformation can in particular be used to determine a degree of similarity (or similarity measure, see above) between a first and a second dataset (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can in particular be determined on the basis of a determined correlation between the first and second datasets.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is in particular part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A navigation system is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

The movements of the treatment body parts are in particular due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. Analytical devices use imaging methods in particular and are in particular devices for analyzing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (and in particular of internal structures and/or anatomical parts of the patient's body) by analysing the body. Analytical devices are in particular used in medical diagnosis, in particular in radiology. However, it can be difficult to identify the treatment body part within the analytical image. It can in particular be easier to identify an indicator body part which correlates with changes in the position of the treatment body part and in particular the movement of the treatment body part. Tracking an indicator body part thus allows a movement of the treatment body part to be tracked on the basis of a known correlation between the changes in the position (in particular the movements) of the indicator body part and the changes in the position (in particular the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (in particular, a fixed relative position relative to) the position of indicator structures (such as the thoracic wall, for example true ribs or false ribs, or the diaphragm or intestinal walls, etc.) which in particular change their position due to vital movements.

The present invention relates to the field of controlling a treatment beam. The treatment beam treats body parts which are to be treated and which are referred to in the following as "treatment body parts". These body parts are in particular parts of a patient's body, i.e. anatomical body parts.

A treatment beam treats body parts which are to be treated and which are referred to as "treatment body parts" or "target regions". These body parts are in particular parts of a patient's body, i.e. anatomical body parts. Ionizing radiation is in particular used for the purpose of treatment. In particular, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating cancer in particular, parts of the body comprising a pathological structure or tissue such as a tumour are treated using ionizing radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. Analytical devices in particular are used to generate the image data in apparatus-based imaging methods. The imaging methods are in particular used for medical diagnostics, to analyze the anatomical body in order to generate images which are described by the image data. The imaging methods are also in particular used to detect pathological changes in the human body. However, some of the changes in the anatomical structure, in particular the pathological changes in the structures (tissue), may not be detectable and in particular may not be visible in the images generated by the imaging methods. A tumour represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernible in the image generated by the imaging method. In addition to these tumours, referred to as "enhancing" tumours, it is thought that approximately 10% of brain tumours are not discernible on a scan and are in particular not visible to a user looking at the images generated by the imaging method.

DESCRIPTION OF THE FIGURES

In the following, the invention is described with reference to the enclosed figures which represent at least preferred embodiment of the invention. The scope of the invention is however not limited to the specific features disclosed in the figures and described in connection with the figures.

Figure 1:
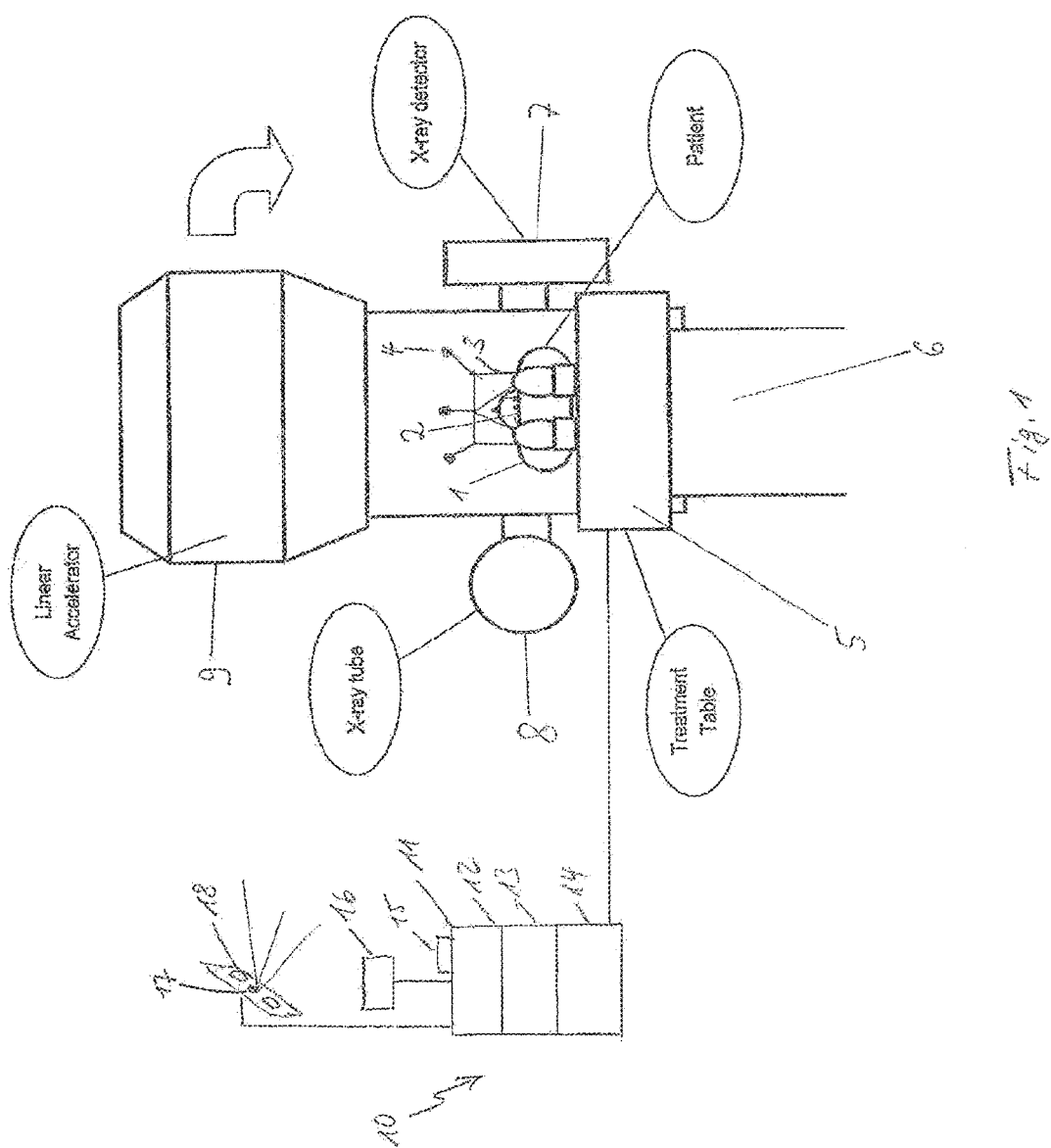
FIG. 1 shows a treatment device usable for conducting the invention.

According to FIG. 1, the treatment device (which can be a radiotherapy or radiosurgery device) comprises at least a patient support device embodied by a treatment table 5, an imaging unit comprising an x-ray tube 8 and an x-ray detector 7, and a treatment unit embodied by a linear accelerator 9 which is configured to emit a treatment beam comprising ionizing treatment radiation onto the anatomical body part represented by the patient's lung 2. A patient 1 having the anatomical body part is placed on the patient support device embodied by the treatment table 5 which can be moved by a moving unit embodied by an electric motor 6. The treatment table 5 is placed under the treatment unit. The curved arrow indicates that the linear accelerator 9 can be rotated around the patient's longitudinal axis. A headrest 3 made from a carbon material is placed adjacent to (in particular under) the patient's head in order to support the patient's head. The base plate of the headrest 3 is shown in FIG. 1 out of perspective and merely for reasons of illustration. A marker device (for example in the shape of a frame or a belt) comprising a plurality of markers 4 is disposed on the patient's thorax, in the case of FIG. 1 three markers 4a are used. The spatial relationship between the markers 4 and the headrest 3 is known and fixed. The treatment device also comprises a computer 11 which is part of a navigation system 10. The computer 11 comprises a volatile memory such as a RAM 14, a non-volatile memory embodied by a hard disc 13 and a processing unit embodied by microprocessor 12. Furthermore, the computer 11 is operatively coupled to an input unit embodied by a keyboard 15 and a visual output unit such as a monitor 16. The navigation system also comprises a transmitter of the navigation system embodied by infrared transmitters 17 and a receiver embodied by infrared-sensitive stereoscopic camera 18 which are both operatively coupled to the computer 11. The computer 11 is also configured to control the other parts of the treatment device such as the imaging unit and the treatment unit and the moving unit. The treatment unit is operatively coupled to the computer 11 in order to receive, from the computer 11, control signals for activating the treatment beam in dependence on the current movement phase data as explained above.

Figure 2:
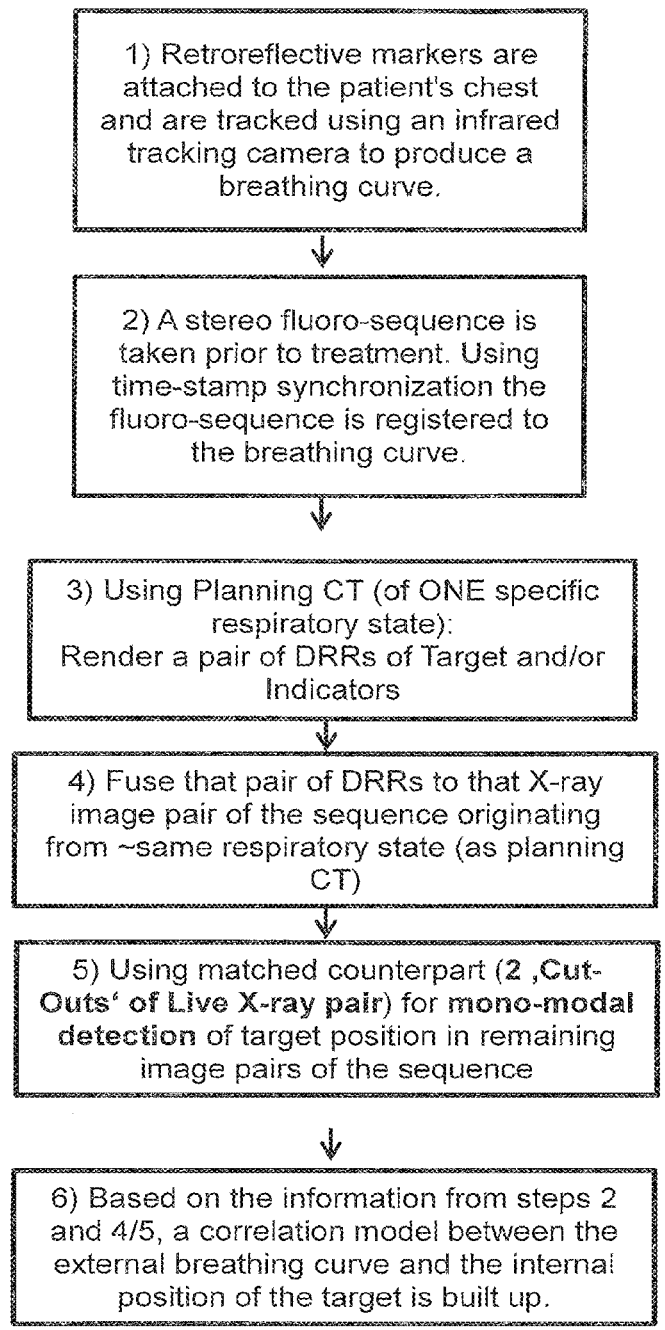
FIG. 2 is a flow diagram showing the functionality of the method in accordance with the invention.

FIG. 2 shows a flow diagram comprising exemplary steps of the above-described data processing method.

Figure 3A:
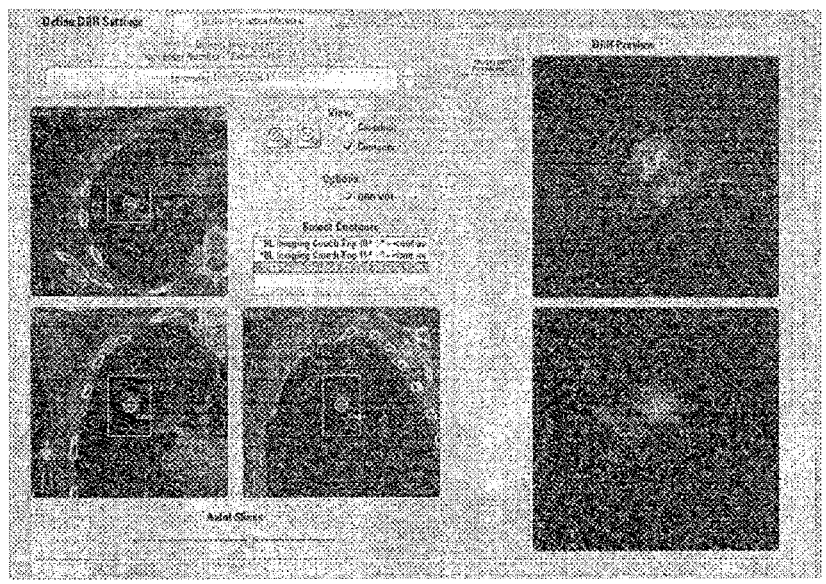
FIGS. 3A to 3C show screenshots from a prototype software application implementing the disclosed method.
Figure 3B:
Figure 3C:
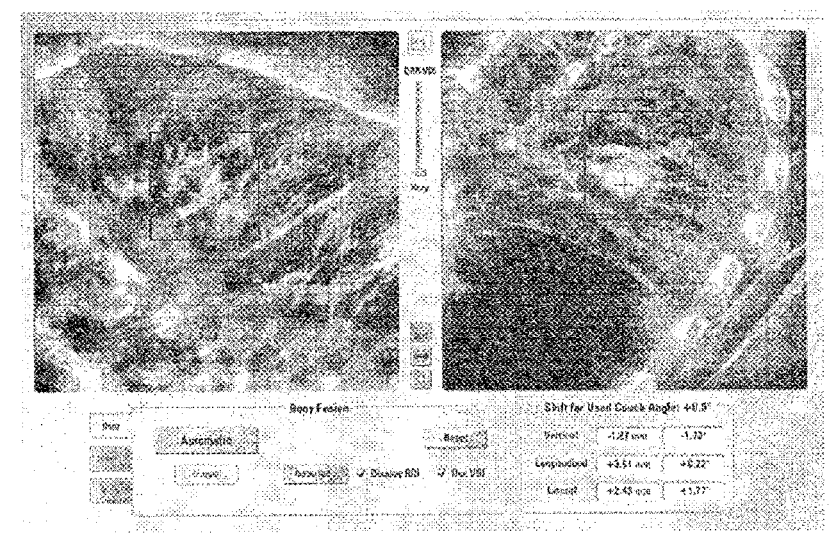

In the flow diagram of FIG. 2 and the screenshots of FIGS. 3A to C, the anatomical body part is a lung tumour and the vital movement is the breathing movement of the patient's thorax.

In particular, steps 1) and 2) relate to generating and acquiring the advance medical image data embodied by a stereo-fluoro-sequence (i.e. sequence of pairs of fluoroscopic images which have been taken in particular in directions which—in three-dimensional space—are perpendicular to each other). In step 1), retroreflective markers are attached to the patient's chest and tracked using an infrared tracking camera 18 to produce a breathing curve for the patient 1. In step 2), the stereo-fluoro-sequence is taken prior to the treatment. Time-stamp synchronization is used to time-correlate the current medical image data embodied by the fluoro-sequence. Thereby, the fluoro-sequence is registered to the breathing curve.

In step 3), the advance medical image data is acquired. In the case of FIG. 2, a planning CT of only one specific respiratory state (i.e. specific movement phase) is used as the advance medical image. From the planning CT, a pair of digitally radiographs (DRRs) of the target region and/or indicators for the position of the target region are rendered. These DRRs are fused in step 4) to that x-ray image pair in the stereo-fluoro-sequence (which embodies the sequence of current medical images) which originates from the at least substantially same respiratory state as the respiratory with which the planning CT is associated. Step 5) encompasses determination of the specific image subset data and the subset tracking data by using a matched counterpart embodied by two selections, e.g. cutouts (clippings), from the x-ray image pair for mono-modal detection of the target position (i.e. of the position of the target region) in the remaining image pairs (i.e. in the remaining current medical images), in particular in the at least one tracking current medical image of the sequence of current medical images embodied by the fluoro-sequence.

Optional step 6) relates to building a correlation model between the external breathing curve generated for generating the advance medical image data (the planning CT and the internal position of the target region which may be embodied by the anatomical body part). Thus, an internal breathing curve can be established. Such an internal breathing curve may serve as a basis for issuing the control signals to the treatment unit for activating or de-activating the treatment beam.

FIGS. 3A to 3C are screenshots gathered from a prototype software application for implementing the disclosed data processing method. FIG. 3A shows in its left half three views from three different spatial directions in which the specific image subset is defined for example by manually clipping a rectangular region in the centre of one of the views, i.e. by user input. The application automatically clips a corresponding region in the two other views by transformation of the coordinates from the manually edited view into the coordinates of the other two views. The three views shown in FIG. 3A are the axial, the coronal and the sagittal view of the planning CT of the tumour. In the right half of FIG. 3A, a preview of a pair of DRRs is given which show a stereo-imaging view of the image region selected (clipped) in one of the views in the left half of FIG. 3A.

FIG. 3B shows a fusion of the DRRs generated as explained with regard to FIG. 3A with the x-ray image pair which has been determined as the specific current medical image. Based on comparing the DRRs to the x-ray image pair, the region in the x-ray image pair representing the specific image subset can be determined and highlighted by placing a rectangular frame around it as shown in FIG. 3C. The rectangular frame shown in FIG. 3C therefore is an example of the above-described graphical feature defined by the display marking data.

The invention claimed is:

1. A medical data processing method of determining a representation of an anatomical body part of a patient in a sequence of medical images, the anatomical body part being subject to a periodic movement of at least one body part of the patient, the method being constituted to be executed by a computer and comprising following steps:
   a) acquiring advance medical image data comprising a time-related advance medical image comprising a representation of the anatomical body part in a first movement phase;
   b) acquiring current medical image data describing a sequence of current medical images, wherein the sequence comprises a first current medical image comprising a representation of the anatomical body part in the first movement phase, and a second current medical image which is different from the first current medical image and comprises a representation of the anatomical body part in a second movement phase which is different from the first movement phase;
   c) determining, based on the advance medical image data and the current medical image data, first image subset data describing a first image subset which is a clipping from the first current medical image, the first image subset comprising the representation of the anatomical body part;
   d) determining, based on the second current medical image from the current medical image data and the clipping from the first current medical image from the specific image subset data, subset tracking data describing a second image subset in the second current medical image, the second image subset comprising the representation of the anatomical body part.

2. The method according to claim 1, comprising a step of acquiring current movement phase data describing a current movement phase of the anatomical body part in states in which it is described by the sequence of current medical images,
   wherein the current movement phase data is generated based on acquiring digital signals describing the periodic movement which have been generated based on tracking marker devices attached to the patient's body and correlating a result of tracking with the current medical image data,
   wherein the first current medical image is determined based on the current movement phase data.

3. The method according to claim 1, wherein the first image subset data describes a position of the first image subset in the first current medical image, and wherein the subset tracking data describes a position of the second image subset in the second current medical image.

4. The method according to claim 2, comprising a step of determining, based on the current medical image data and the subset tracking data and the current movement phase data, internal breathing curve data describing a time-correlation of the image positions of the anatomical body part and the sequence of current medical images.

5. The method according to claim 1, wherein the first image subset data is determined based on determining a corresponding representation of the anatomical body part in the advance medical image and in the sequence of current medical images.

6. The method according to claim 1, comprising a step of acquiring current medical image user input data describing an input by a user for selecting the first image subset from the first current medical image wherein the first image subset data is determined based on the user input data.

7. The method according to claim 1, comprising a step of acquiring advance image subset data describing an advance image subset of the advance medical image comprising the representation of the anatomical body part, wherein the first image subset data is determined based on the advance image subset data.

8. The method according to claim 1, comprising a step of acquiring advance medical image user input data describing an input by a user for selecting the advance image subset from the advance medical image, wherein the advance image subset data is determined based on the advance medical image user input data.

9. The method according to claim 7, wherein the first image subset data is determined based on the result of comparing the advance image subset data to the first current medical image.

10. The method according to claim 1, wherein the subset tracking data is determined by determining a region in the second current medical image which is at least to a predetermined degree comparable to the first image subset.

11. The method according to claim 1, wherein the advance medical image data has been generated by applying a computed tomography imaging method to the patient's body, wherein the advance medical image is in particular a digitally reconstructed radiograph reconstructed from the computed tomography of the patient's body, and wherein the sequence of current medical images has been generated by applying a conventional x-ray imaging method.

12. The method of claim 1, wherein determining, based on the second current medical image from the current medical image data and the clipping from the first current medical image from the specific image subset data, the subset tracking data comprises:
  determining the subset tracking data based on analyzing pixel coordinates in the second current medical image having same values as pixel coordinates of the first image subset which is the clipping from the first current medical image, that determines a degree of similarity.

13. The method of claim 1, wherein determining, based on the second current medical image from the current medical image data and the clipping from the first current medical image from the specific image subset data, the subset tracking data comprises:
  determining the subset tracking data based on comparing the first image subset which is the clipping from the first current medical image to total image information contained in the second current medical image.

14. A non-transitory computer readable program storage medium on which the method according to claim 1 is stored and configured to be executed by at least one processor of a computer.

15. A treatment device, comprising:
  a) a computer comprising the program storage medium according to claim 14;
  b) a medical imaging device for acquiring current medical image data;
  c) an irradiation unit for emitting a treatment beam to a patient's body,
  d) wherein the computer is operatively coupled to the medical imaging device to acquire the current medical image data and to the irradiation unit to issue control signals for emitting the treatment beam.

* * * * *